United States Patent
Hirtt et al.

(10) Patent No.: US 8,464,592 B2
(45) Date of Patent: Jun. 18, 2013

(54) METHOD AND APPARATUS FOR DETERMINING VOID VOLUME FOR A PARTICULATE MATERIAL

(75) Inventors: Pierre Hirtt, Luxembourg (LU); Yves Leiner, Kayl (LU)

(73) Assignee: HITEC Luxembourg S.A., Luxembourg (LU)

( * ) Notice: Subject to any disclaimer, the term of this patent is extended or adjusted under 35 U.S.C. 154(b) by 279 days.

(21) Appl. No.: 12/895,448

(22) Filed: Sep. 30, 2010

(65) Prior Publication Data

US 2011/0079087 A1   Apr. 7, 2011

Related U.S. Application Data

(60) Provisional application No. 61/278,218, filed on Oct. 2, 2009.

(51) Int. Cl.
*G01N 3/08* (2006.01)
*G01N 3/00* (2006.01)

(52) U.S. Cl.
USPC .......................................................... 73/818

(58) Field of Classification Search
USPC .......................................... 73/818, 820, 825
See application file for complete search history.

(56) References Cited

U.S. PATENT DOCUMENTS

| | | | | |
|---|---|---|---|---|
| 3,917,781 A | * | 11/1975 | Gabriel et al. | 264/71 |
| 4,311,672 A | | 1/1982 | Kallenberger | |
| 4,891,993 A | * | 1/1990 | Barker | 73/863.52 |
| 5,039,294 A | * | 8/1991 | Gautier et al. | 425/149 |
| 5,087,398 A | * | 2/1992 | Le Molaire et al. | 264/40.5 |
| 5,760,293 A | | 6/1998 | Orr | |
| 6,002,790 A | * | 12/1999 | Horvath et al. | 382/141 |
| 6,924,484 B1 | * | 8/2005 | Wang et al. | 850/9 |
| 7,167,240 B2 | | 1/2007 | Stagg | |
| 7,187,441 B1 | | 3/2007 | Sevick-Muraca | |
| 7,722,713 B2 | | 5/2010 | Green | |
| 2003/0113397 A1 | * | 6/2003 | Bald | 425/412 |

OTHER PUBLICATIONS

George A. Joyce, et al, "Advances in Structure Measurements of Carbon Black", Rubber World, Sep. 1, 2009.
Probst, "Structure and Electrical Properties of Carbon Black", Carbon, Elsevier, Oxford, GB, vol. 40, No., Feb. 1, 2002, pp. 201-205.

(Continued)

*Primary Examiner* — Max Noori
(74) *Attorney, Agent, or Firm* — George W. Moxon, II; Brian P. Harrod

(57) ABSTRACT

An apparatus for and method of measuring the compressed volume of a particulate material comprising a chamber for containing a particulate material which will be evaluated; a removable, fixed means at one end of said chamber to enclose said chamber and for containing said particulate material within said chamber; a compression means at the other end of said chamber which further encloses and contains said particulate material within said chamber and which provides a linear force on said particulate material so that one end of said particulate material is linearly movable and said compression means will compress the particulate material in said chamber; means to move said moveable piston away from a particulate material placed inside said chamber to decompress the particulate material in said chamber; means for measuring the distance between said movable piston and said fixed means so to measure the thickness of said compressed particulate material; and measuring means on the moveable piston of said chamber for measuring the applied force of said piston to said particulate material when said piston is compressing said particulate material.

16 Claims, 9 Drawing Sheets

OTHER PUBLICATIONS

Micromeritics: "Dynamic Void Volume Analyzer 4000", Retrieved Mar. 31, 2011 online at: http://www.micromeritics.com/Product-Showcase/Digital-Void-Volume-Analyzer-4000.aspx.
Micromeritics: "Micromeritics to Showcase New Instruments at Pittcon 2007—Feb. 23, 2007", Retrieved Mar. 31, 2011 online at: http://www.micromeritics.com/Pressroom/Press-Release-List/Micromeritics-to-Showcase-New-Instruments-at-Pittcon-2007.aspx.
ASTM International, "D6086-09a", Jul. 1, 2009.

* cited by examiner

METHOD AND APPARATUS FOR DETERMINING VOID VOLUME FOR A PARTICULATE MATERIAL

PRIORITY CLAIM

The present application claims the priority of U.S. Provisional Filing Ser. No. 61/278,218, filed Oct. 2, 2009, which is incorporated herein by reference.

BACKGROUND OF THE INVENTION

The present invention is related to a method and apparatus for measuring the structure of powder materials, and in particular rubber fillers, such as carbon black and silica. The method and apparatus measures both the compression and decompression of samples of the powder materials in a controlled way to understand the volume and pressure curves.

Carbon black and silica are prime materials for rubber production and are used as fillers or additive materials, such as reinforcing materials in polymer compounds. The structure of these materials is a physical property that is a result of the macroscopic shape of the carbon or the silica particle arrangement. The structure influences the properties of the final product. For example, when used in rubber, the properties influenced include hardness, softness, elasticity, stiffness, dispersibility, viscosity, abrasion resistance, loss angle, and the like. Particle size also determines the surface area of the particles and this can also affect the properties of the final product.

The determination of structure of powders includes their void volume and properties and their ability to be compounded with rubbers and plastics. The carbon black and rubber industry has looked for several decades for a way to determine the same material property by compressing the subject material to a high pressure and then determine the specific volume that the sample takes under pressure, and finally correlate this volume to the quantity of oil that the material is able to absorb. The applicable standard is ASTM D6086, although there is no consensus on the appropriateness of the method described therein.

Structure is a central characteristic of particulate matters and granulates, e.g. rubber filler materials such as carbon black or silica. Structure is a generic term that describes the shape irregularity, the deviation from sphericity and the aggregation or agglomeration of particles. The higher the structure of a certain material is, the higher will be the volume occupied by a certain mass of this material and the more void volume will be included within a sample. Some phenomena that contribute to structure are very stable, others can easily be altered. In the case of carbon black, structure decreases when agglomerates are mechanically broken down to aggregates. For silica, a chemical reaction that reduces structure can be mechanically induced.

A number of instruments for testing to determine the so-called "structure" of rubber fillers according to traditional methods which have been standardized by ASTM International (originally known as the American Society for Testing and Materials) are available on the market. One established method uses oil, such as DBP (or n-Dibutyl-Phthalate) or paraffin as a liquid to be absorbed and is based on the determination of the saturation point for the material to absorb oil. This will generate an oil absorption number (or OAN). When the sample is then compressed in order to break part of the structure prior to determining the saturation point of the oil absorption, a compressed oil absorption number (or COAN) is generated. The applicable standards include ASTM D2414 and D3493, as well as ISO4656 for carbon black, and ASTM D6854 for silica. The basic approach for determining void volume (VV) goes back about 10 years and is presented in ASTM standard D6086. The void volume is calculated from the sample volume according to the ASTM standard D6086.

The Micromeritics Instrument Corporation sells its instrument DVVA 4000 which is a dynamic void volume analyzer capable of measuring the compressed void volume and density of powders. The instrument tests the sample by compressing the sample either in a constantly increasing pressure mode or in a step-wise fashion to a pressure up to 230 MPa (33 kpsi). During compaction, the change in volume or density is monitored as a function of pressure, thus allowing the compacting behavior of the material to be characterized. The difference between the initial apparent volume and the final apparent volume expresses the reduction in (void) volume as a result of compression and the difference between the apparent volume and the skeletal volume is the void volume.

Like Micromeritics, other companies also analyze powders using only a compression curve, i.e. the shape of the curve from zero pressure to a certain maximum pressure. Typically, these companies use compressing cylinders having a diameter of 12.7 mm (0.5 inches).

The approach to find new methods of analyzing powder to understand their properties have been driven by the fact that the oil absorption tests are not clean tests because of the material involved, tedious and often only poorly correlated to the properties of the end product. But since the oil absorption test has been considered the standard, any new test must correlate the oil absorption measurement to the compressed volume measurement. The reasoning in the oil absorption test is that the oil would take the free space between the aggregates and only this free space, and of course not the absolute (entire) volume of the sample. Thus, the volume of the material itself is deducted, such that the absolute volume minus the material volume is the "void volume". Industry uses as specific density value of 1.90 g/cm$^3$ for carbon black. Since the difference of the absolute volume and the void volume is a fixed offset value, they are mathematically equally valid as a measure of structure and for the correlation to oil absorption numbers.

SUMMARY OF THE INVENTION

The present invention determines the structure of carbon black and other rubber fillers or other powder material for which structure is an important material characteristic by measuring accurately the compression and decompression curve of the material. The currently common measure of structure, i.e. the oil absorption number of compressed sample, is correlated linearly to the residual void volume of the material after decompression. The residual void volume is determined from the intersection of a mathematical fit of the last part of the decompression curve with a certain pressure value, which is offset to the residual pressure.

The method of the present invention involves the steps of compressing a powder sample, measuring the thickness of the powder sample and the force applied, calculating the resulting volume and then deducting the theoretical volume of the sample mass, and then determining the void volume that remains between the aggregates which comprise the material. This measure represents the so-called material structure as function of pressure. This allows for the selection of fillers of varying structure and their use in varying the rubber properties based upon the powder structure.

With the same measurements, an additional key characteristic can be determined. During a compression-decompression cycle, a certain amount of energy is put into the sample. This work is essentially the energy required to bring the sample into the residual void volume state, where part of its structure is broken up. This work, which is a measure of stability of the structure, can be related to softening effects that can be observed in rubber compounds, which are also due to disruptions of the filler-filler networks.

BRIEF DESCRIPTION OF THE DRAWINGS

The present invention will now be described by the way of a non-limiting example, with reference to the attached drawings in which.

DETAILED DESCRIPTION OF THE INVENTION

The present invention determines the structure of carbon black and other rubber fillers or other powder material for which structure is an important material characteristic by measuring accurately the compression and decompression curve of the material. The currently common measure of structure, the COAN, is correlated linearly to the residual void volume of the material after decompression. The residual void volume is determined from the intersection of a mathematical fit of the last part of the decompression curve with a certain pressure value, which is offset to the residual pressure.

The void volume methods of extracting equivalent structure information developed so far try to determine the material property at a physical condition (compressed state) that is not the same or not even similar to the material's physical condition as in COAN measurements or in the end product. Processed into the rubber compound or during oil absorption measurements, the material is at near ambient pressure.

The present invention has found a correlation to this material characteristics at the end of a certain full compression and decompression cycle, i.e. when the material is again in a physical condition that is the same or at least sufficiently similar to the material in the standardized measurement approach (COAN according to ASTM and ISO standards).

Figure 1:
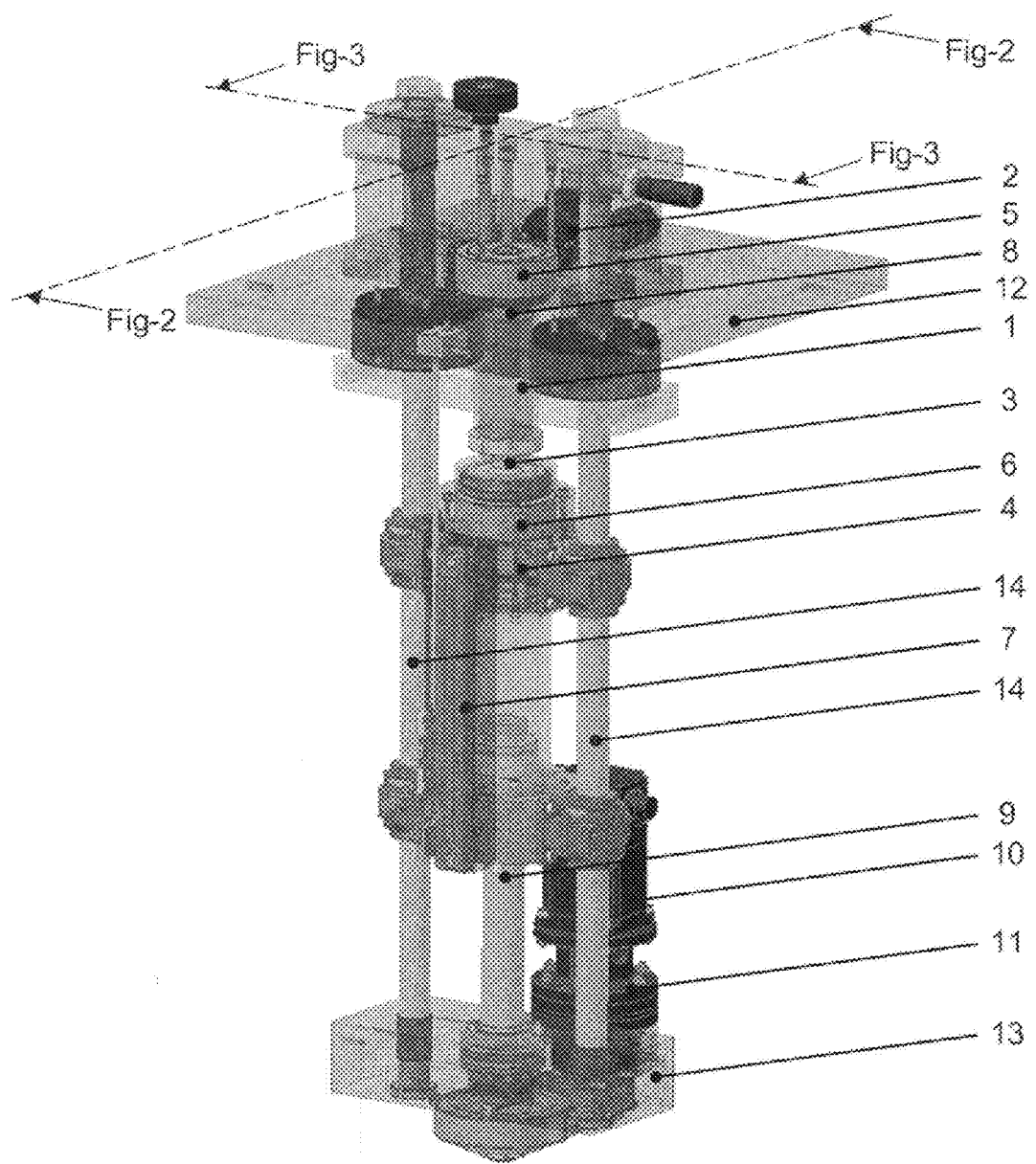
FIG. 1 a schematic picture of the apparatus of the present invention.
Figure 2:
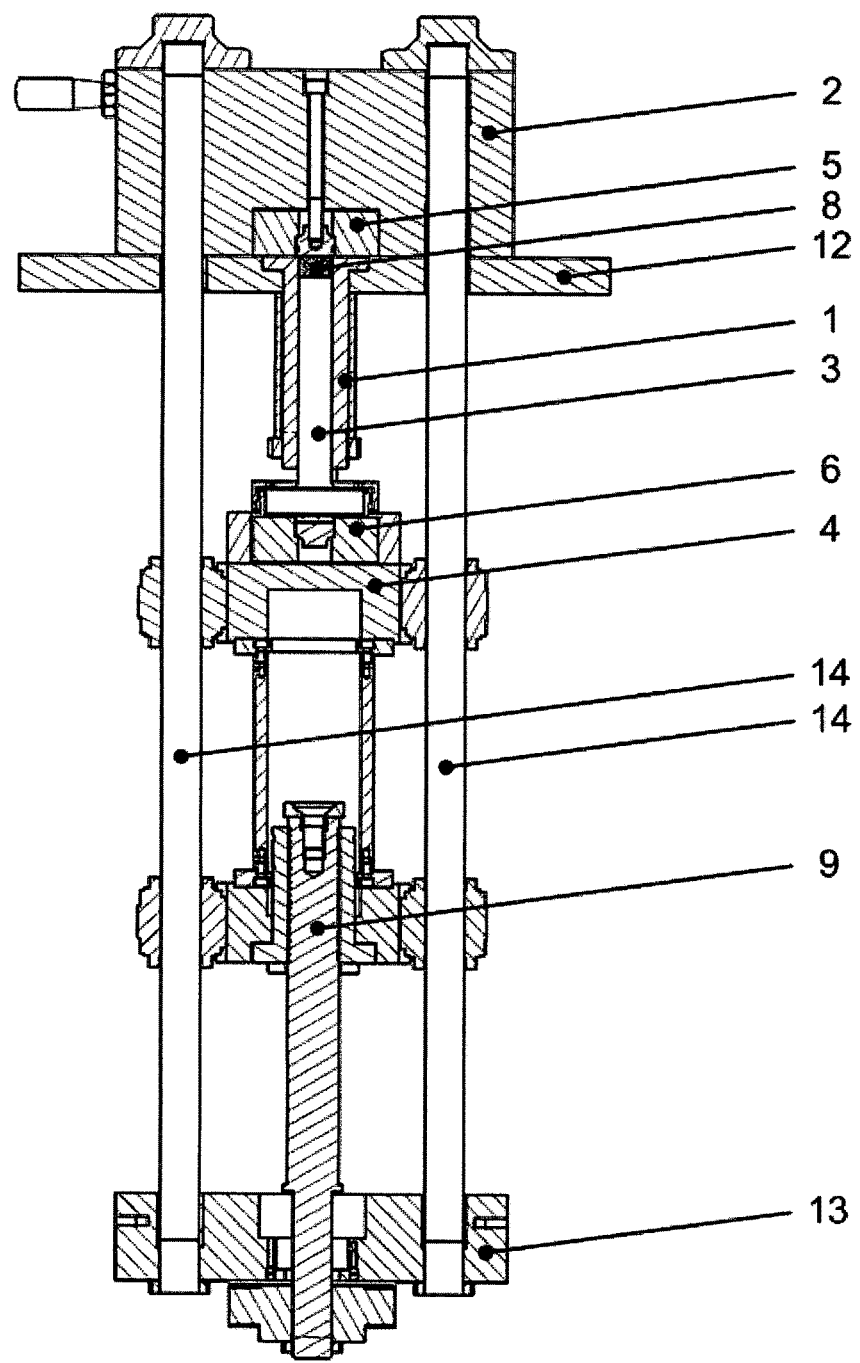
FIG. 2 a cross sectional view of the apparatus of FIG. 1 along lines 2-2
Figure 3:
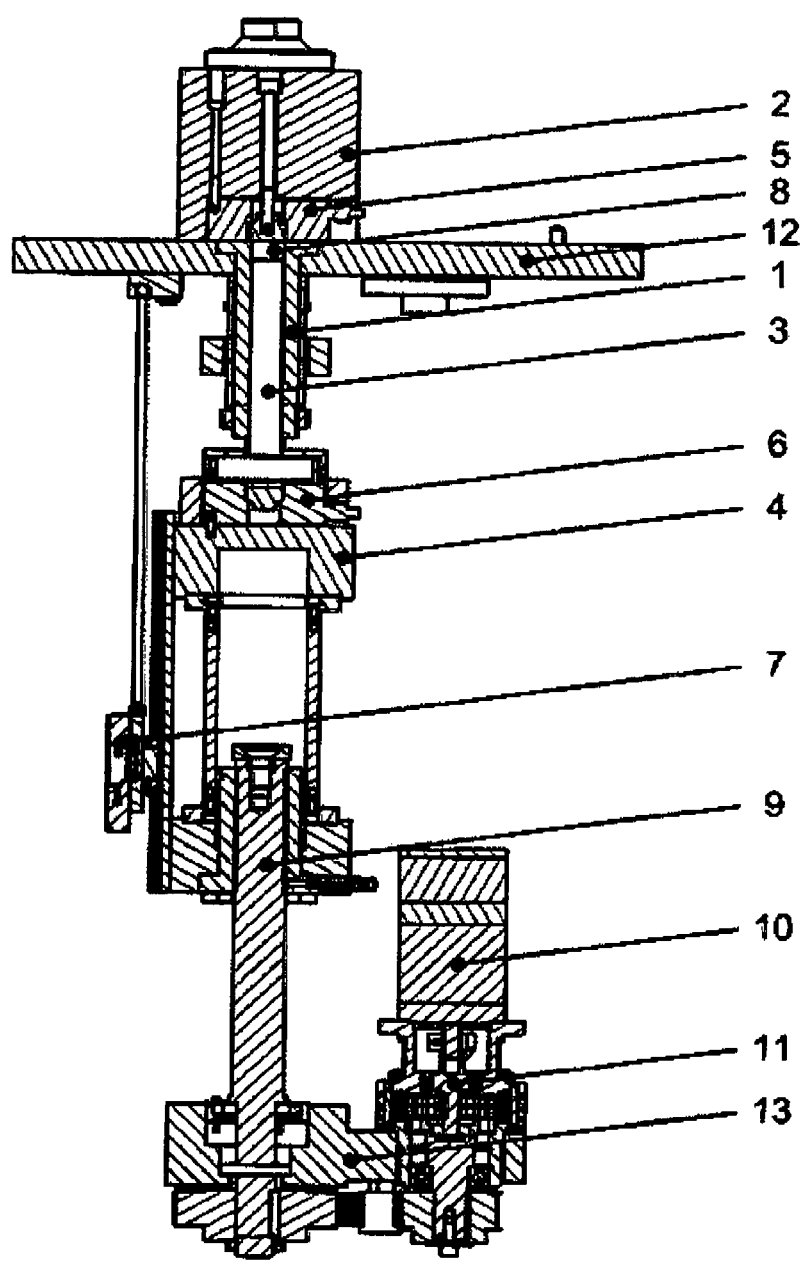
FIG. 3 a cross sectional view of the apparatus of FIG. 1 along lines 3-3
Figure 4:
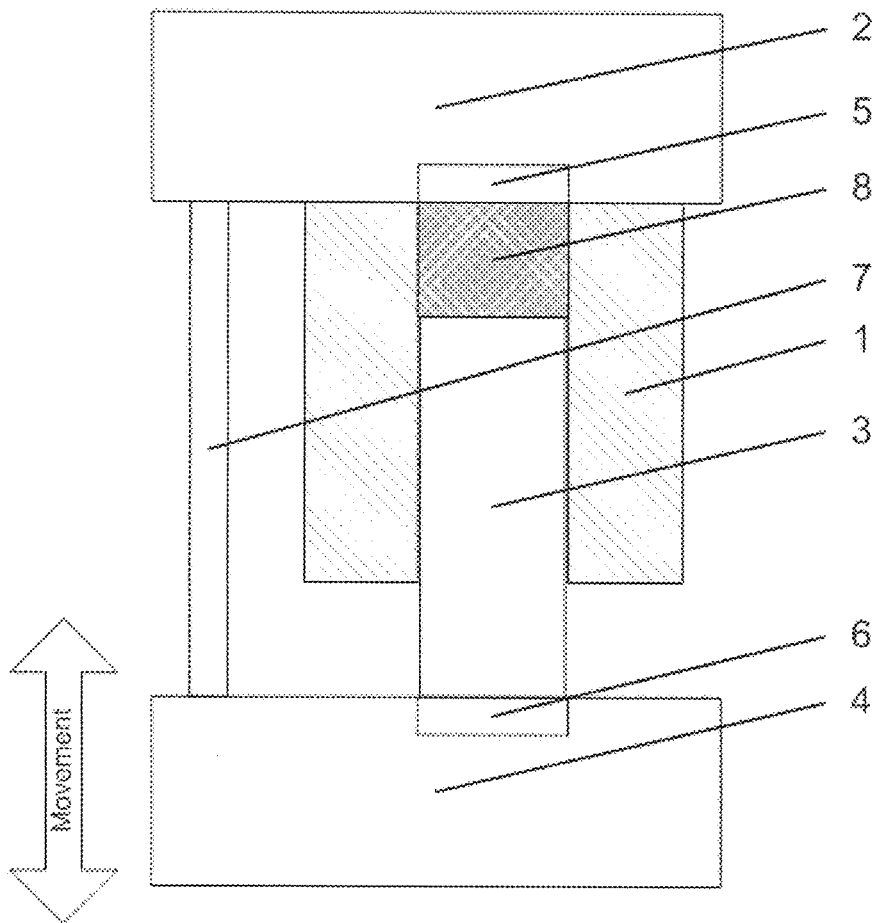
FIG. 4 is a block diagram of the components of the apparatus shown in FIG. 1
Figure 5:
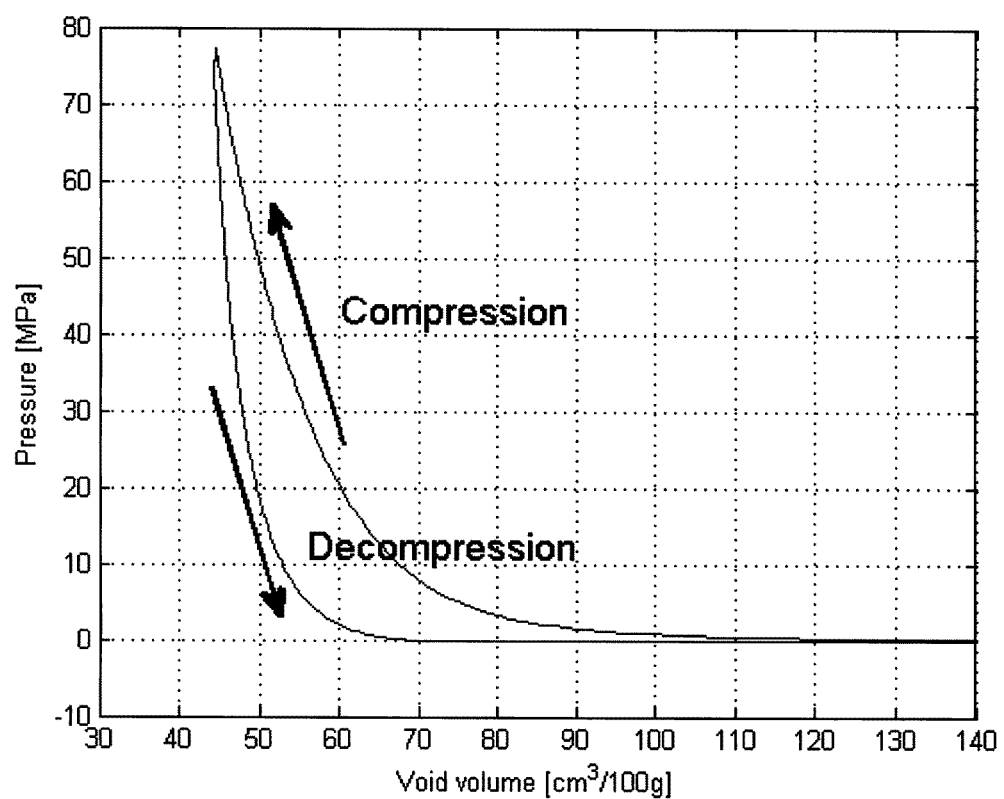
FIG. 5 shows typical compression and decompression curves for powder samples.

The apparatus or instrument of the present invention allows for the accurate determination of the materials volume during compression and during decompression. The compression and decompression speed is freely programmable and is controlled by appropriate hardware and software, such that conditions can accurately be produced and re-produced. A typical compression and decompression curve expressed in void volume is illustrated in FIG. 5.

Compressing the material has an irreversible effect on the material. It is known in the appropriate industry that shear energy, as produced by mixing these fillers into rubber polymers or by compressing it, will break some of the agglomerates that form the material; hence reduce the "structure" since size and shape of the agglomerates and aggregates quantify the structure of the material. It is further known in the appropriate industry that carbon black does not change chemically when applying such mechanical shear and/or compression forces. And it is known in the appropriate industry that the shape of the carbon black aggregates is a result of the manufacturing process and does not change later. Only the size of the agglomerates can be affected by shear forces (a larger agglomerate can break and form two smaller agglomerates or aggregates). This has been demonstrated by electron microscopy analysis.

Figure 6:
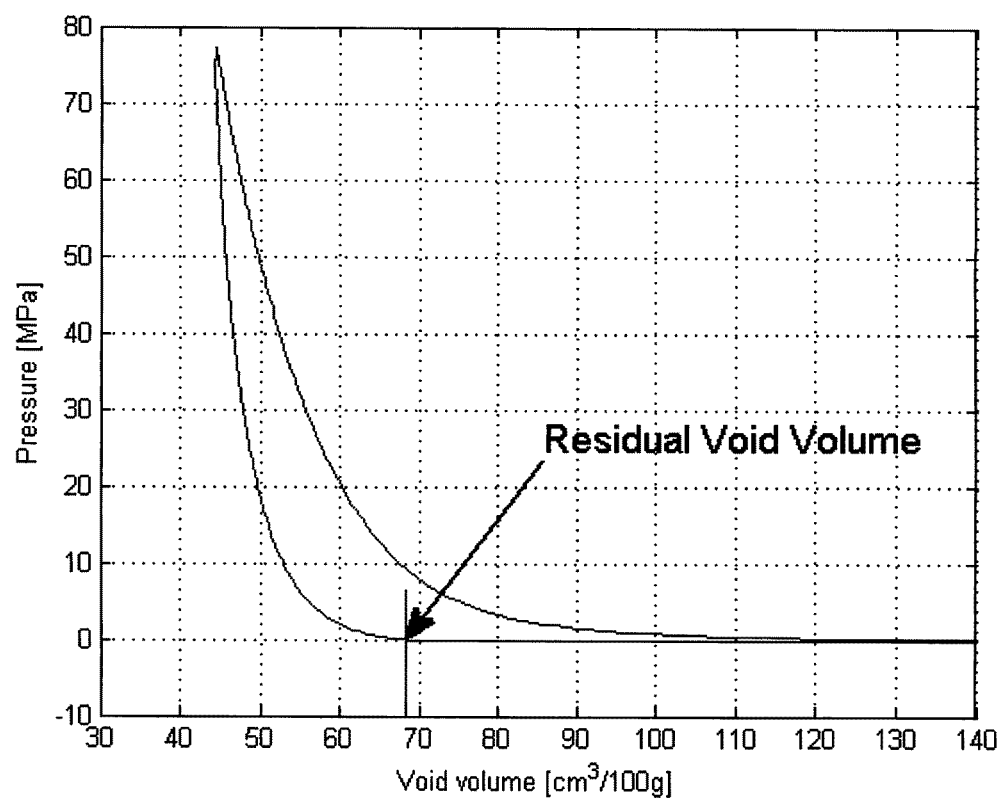
FIG. 6 shows compression and decompression curves which establish the residual void volume of a powder sample.

One would expect that the compressed material will not reverse back after decompression to the same volume than the initial volume of the "virgin" material. Our experimental efforts confirmed our observations. At the end of the compression and decompression cycle, all aggregates will have taken the minimum space that the material can have at ambient pressure, i.e. all aggregates, as sized after a given compression, have taken a closest possible position to each other. This results in the residual void volume as illustrated in FIG. 6.

Second, one would expect that the pressure, as measured on the moving cylinder, drops down to zero and that the transition from a pressure that is greater zero ($p>0$), to the zero pressure level ($p=0$) could be clearly seen at the moment when the material is fully expanded to zero pressure (i.e. its residual volume), and when the moving cylinder looses contact with the material.

The latter is however clearly not the case for carbon black. Our observation is that the decompression curve for carbon black converges asymptotically against zero without any discontinuity. A discontinuity could for example be visualized on the derivative of the pressure curve with respect to void volume. Such discontinuity would indicate the transition from the loaded moving piston, to lose contact with the material, and the pistons position at that moment would then enclose the residual volume of the material. Again, such discontinuity cannot be observed on carbon black but the curves converge asymptotically against zero. Such asymptotic decompression behavior may not be limited to carbon black, but may also occur for other powder materials.

As such and because of its continuous transition, the decompression curve for this material does not provide a "clear signal" of what could be used to quantify the residual void volume after complete decompression, which in turn correlates to the structure values as defined today, and/or quantifies the absolute structure of the material.

The above statements, which are valid for the decompression curve as measured on the moving piston and which converges normally against zero pressure, is also valid for a pressure sensor that is mounted on the opposite side in the compression chamber, i.e. the closing stationary cover of the compression chamber. In this case the decompression does not converge to zero pressure but to a residual pressure greater than zero, which amount depends on the grade, i.e. different material converge for given geometrical dimensions of the compressing cylinder to a different residual pressure.

For silica, which is the second most important rubber filler, it is generally known in the appropriate industry that, at sufficiently high pressure a chemical reaction takes place that changes part, but not all of the molecular composition of silica. This results in a change of the chemical properties of these silica molecules. The molecules form particles (not necessarily spherical) and aggregates. During said process, water molecules become free. This process may change the shape of the aggregates. In other words, these materials change their chemical and physical properties due to the chemical reactions that are initiated by the applied pressure. In addition, the compression and decompression cycle also causes change of the material structure due to simple mechanical breaking of subject aggregates. Hence, there are physical and chemical changes that affect the structure for these materials.

For silica materials, we could at this moment already observe that the decompression from fairly high pressures results in a clear instant change of the curve when it reaches zero pressure, resulting in a discontinuity of the derivative of the decompression curve.

Since carbon black and other powder material do not change chemically, they have the "inconvenience" of not generating a clearly visible indication for the "end of decompression"; which identifies the residual volume. The method of present invention facilitates obtaining a value for the residual void volume from the asymptotic decompression curve. This method uses an algorithmic approach, such that it can be programmed in a computer code and applied by the computer code for any material, i.e. without "calibrating" the specific material. So, the analysis is done using a computer or processor which performs the calculations based upon the algorithms which convert the sample thickness values into void volume values at any given pressure. For each material, it has to be verified that its decompression curve can be described sufficiently well by a specific mathematical function. With the mathematical fit function, which typically is an exponential fit, a parametric fit is performed on the decompression curve. A check of the "goodness", i.e., that it fits well enough as to the response of the measured points, of the fit is performed automatically by a programmable algorithm. In order to do so, the coefficient of determination $R^2$ between model (i.e., the exponential function) and the measurement data is calculated. If the coefficient of determination is found to be higher than the threshold value, then the fit is considered as good. An acceptable value for the threshold has been found to be 0.99.

A programmable algorithm automatically determines the residual pressure, which is zero or close to zero at the moving cylinder, but is greater zero at the opposite site, i.e. at the stationary cover. A programmable algorithm automatically reads the residual void volume at the intersection of the mathematical fit that describes the decompression curve, and a certain offset to the residual pressure. The value of this offset can be varied such that the observed residual void volume changes; with increasing offset the void volume values decrease. It is possible to change this offset value within a certain range, such that for any offset within this range, the resulting residual void volume values for various materials, correlates well with the classically observed structure values. The observed correlation for carbon black is linear.

Figure 8:
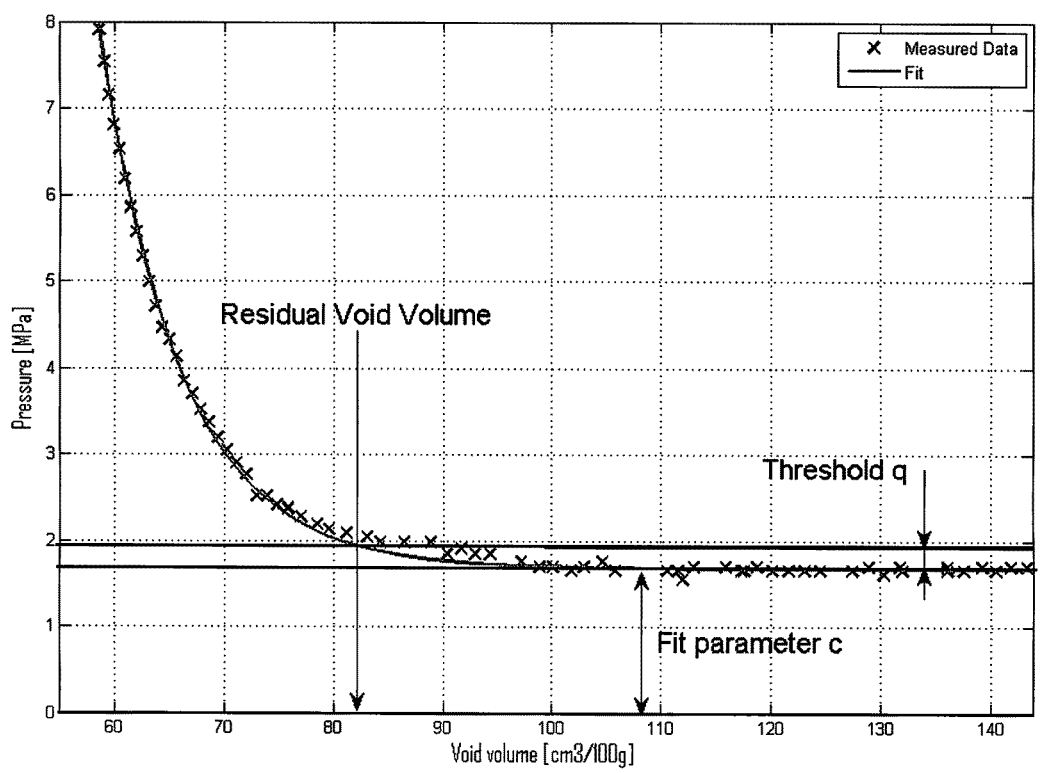
FIG. 8 is a graph to illustrate fit parameter c and threshold q as pressure value to intersect with the mathematical exponential function.

The mathematical description of the above observation is described below and is illustrated in FIG. 8. The transition region during decompression, i.e., where the piston is moving away from the fixed end but is still in touch with the sample, and the region where the piston is not in contact with the sample any more can well be fitted using an exponential function:

$$p = a * \exp(b * VV) + c$$

where p is the pressure, VV is the void volume and a, b and c are the fit parameters, which are determined by using least squares nonlinear regression analysis on the data points for the void volume as a function of the pressure during decompression, with void volume as the independent variable. The parameter c can physically be interpreted as the residual pressure on the sensor (depending on the sensor position c can be zero).

The method for determining the residual void volume on such a smooth curve consists in finding the void volume where the pressure comes closer to its final value c, than a certain threshold (offset) value q:

$$p - c = a * \exp(b * VV) = q$$

As such, the residual void volume is calculated using the following equation:

$$VV_{res} = 1/b * \log(q/a)$$

wherein the threshold (offset) q must be kept constant when comparing different materials.

The present invention is useful to measure the so-called structure of rubber fillers. By applying this mathematical fit to the curves, we can now determine the residual void volume with one and the same programmable algorithm, and we can correlate it with a simple linear function to the industry established COAN method (ASTM standard D3493).

The present invention is related to a metrological instrument for determining the void volume of particulate matters and granulates. The measurements are based on the ASTM standard D6086, with these additional features:

The carbon black sample is compressed to a target pressure in a controlled way.

The carbon black sample is decompressed in a controlled way until the compression piston leaves contact with the sample.

Volume and pressure are recorded continuously.

Pressure can be recorded on the static or moving side of the sample.

The test method is not limited to carbon black.

During the decompression, the carbon black sample expands such that at the end it has a well defined residual void volume, different from both the initial void volume and the minimum void volume during compression. The compression-decompression cycle eliminates the unstable contributions to the material structure. The residual void volume is thus a measure of the stable part of the structure only, and could be used for predicting material characteristics in the processed state.

The residual void volume after the decompression is linearly correlated to the COAN, such that the COAN can be predicted from the residual void volume as determined using the process of the present invention. Before compression in the present invention, as compared to before crushing for the COAN, part of the structure of the carbon black results from fragile agglomerates. After a compression-decompression cycle in the present invention only the stable portion of the structure remains, just as it does after the crushing for the COAN. Thus determining the residual void volume is considered to be physically equivalent to the COAN determination.

The present invention provides a novel method and apparatus or instrument for determining the residual void volume of carbon black after a compression-decompression cycle.

The apparatus is a unique assembly using standard components, including the motor, gearbox, screw jack, load cell, computer, and the like. The apparatus is unique in that it is the only apparatus to measure not only the compression but also the decompression curve.

As can be seen in FIGS. 1, 2, 3, and 4, the apparatus of the present invention consists of a cylindrical compression chamber 1 that is mounted flush in a top table 12. A cover 2 on top side can be opened and closed to load and remove the sample 8 of material to be tested. Two tow bars 14 hold the cover 2 against the top table 12 and the compression chamber 1. The bottom side of the compression chamber is closed by a moveable piston 3 of tight tolerance inside the cylindrical chamber 1 so that no significant amount of sample material is lost under any condition. The losses, if any, are observed to be less than 0.1% of the sample mass. The shape of the compression chamber 1 is shown as cylindrical, but it is not limited to cylindrical, and could be other shapes and geometries. The cylindrical shape is chosen because it is easy to fabricate with tolerances that are as tight as possible, and the calculations which are part of the algorithm are simplified. The tolerances and material combinations of piston and chamber are chosen such that friction to move the piston is as low as possible. An acceptable amount of friction force to move the piston up or down, for an instrument of dimensions as used in this description is about 100 N.

The means for applying force to compress the particulate sample is preferably a linear, moveable piston 3, which is mounted on a traverse 4 and which is guided by tow bars 14 and attached to a mechanical linear actuator 9 that can move the traverse 4 with the compression piston 3 up and down. The mechanical linear actuator 9 is designed to transmit compression force via the traverse 4 and the piston 3 into the sample 8 material. The drive system with appropriate frame and cover will provide up to 170 kN compression force to a sample. The mechanical linear actuator 9 is mounted on a bottom plate 13 with the two tow bars 14 that can transmit the compression force through the bottom plate 13 and the tow bars 14 onto the cover. During a measurement in which a sample of particulate material is compressed, the cover 2 is held closed and as such forms a fixed end of the measuring chamber in which the material is to be tested.

The mechanical linear actuator 9 that holds the traverse 4 with the moveable piston 3 is driven by a backlash free drive train consisting of gearbox 11 and electrical motor 10. The entire drive chain from motor to compression piston allows for a backlash free movement of the piston relative to the fixed cover in both directions, such that the enclosed volume in the compression chamber can be varied by control of the movement of the motor. Standard industrial components are used to control the movement of the drive motor; servo technology and stepper motors have been confirmed to fulfill the requirements.

The traverse 4, which is holding the compression piston 3 and the table 12, which is reference for the fixed end of the compression chamber, are interconnected with a linear measurement system 7 that allows to determine the inside height of the compression chamber up to 0.001 mm resolution. In addition to measure pressure, a force sensor (static) 5 is mounted at the top, terminal end of the compression chamber 1, while a force sensor (moving) 6 is mounted at the bottom, terminal end of the compression chamber 1.

The compression chamber and consequently the compression piston have been chosen cylindrical for ease of fabrication. Other geometries are possible. The present design allows for cylinder diameters from as low as 10 mm or even less, up to 60 mm diameter. Various diameters have actually been fabricated and tested: 12.7 mm (0.5 inch), 25.4 mm (1 inch) and 50.8 mm (2 inches). The design of the buildup allows for up to 150 mm initial height of the compression chamber. This is sufficient and leaves even a margin to fill material of various quantities and various pour density (material of low pour density has a high initial volume per mass). A measuring accuracy of the height of the compression chamber of typically 0.002 mm is considered as being sufficient for the method.

The actual compression force is measured by two independent force sensors. One is mounted under the compression piston and can measure the pressure that is applied to the sample. The second one is mounted in the cover such that its surface forms the fixed end of the compression chamber and it measures the pressure that is transmitted through the sample. The sensors and its acquisition system provide typically a measuring accuracy of 0.5%

The control system has appropriate standard industry hardware to continuously acquire and convert into digital values the position of the piston and the values of the two force sensors. A sampling speed of 1000 readings per second or more, as typically possible with standard data acquisition hardware, is sufficient for the method.

The pressure p of the compressed particulate material is determined using the equation:

$$p = F/(\pi/4 * D2)$$

where D is the diameter of the cylindrical chamber, and where F is the measured force on the moveable piston, respectively on the fixed end.

The actual volume of the sample is calculated using the equation:

$$V(p) = \pi/4 * D2 * h(p)$$

where D is the diameter of the cylindrical chamber, and where h(p) is the height of the inside of the compression chamber; hence the thickness of the compressed material at pressure p as measured on the moveable piston, respectively on the fixed end at any stage of the compression or decompression of the particulate material.

The system is programmable to run the moveable piston at several modes and conditions via the control of the motor. The controller is programmed such that conditions can be selected where the compression piston runs at constant speed (constant piston speed), or where the motor speed is controlled in a closed loop such that the measured pressure increases or decreases by a fixed amount per time (constant pressure rate). The programmable controller is adjusted such that the piston movement, may it be constant or may it depend on the pressure rate, is smooth. Smooth has to be understood such that no discontinuities in the acceleration of the piston movement and no discontinuities in the derivation of the pressure are visible within 10 times the resolution of the data acquisition system (at 1000 Hz or more).

A full measurement of a sample consist of compressing the material up to a maximum pressure that is arbitrarily selected, and then revert the movement of the piston to gradually decompress the material (i.e. release gradually the pressure) from maximum pressure until the compressing cylinder does not touches the sample material anymore. A typical compression and decompression curve is illustrated in FIG. 5.

The best results in terms of resolution of sampling points for numerical treatment have been achieved when running compression and decompression at constant pressure rate. A typical cycle is starting at a position which provides sufficient volume to fill in the sample material. The size (mass) of the sample material may vary for different material. A sample size of approximately 2 grams has proven to be appropriate for carbon black material. The actual size is determined with an accuracy of 0.002 grams, for an instrument of dimensions as used in this description.

A typical cycle starts at zero pressure and then runs the motor at maximum speed until the material starts to be compressed and the pressure increases. The programmable controller will now adjust the speed of the motor such that the pressure increases at the selected rate, i.e. a certain increase of pressure per time unit. When the preselected maximum pressure is achieved, the motor will hold the movement for a preselected time (typically 5 seconds) and then revert its movement to decompress the material such that the pressure decreases at the selected rate, i.e. a certain decrease of pressure per time unit. The test cycle will end when the piston reaches its initial starting position.

Satisfying results could be observed at a wide range of pressure rates, from as low as 0.1 MPa/s up to 3 MPa/s and even more. A reasonable compromise value in terms of quality of measurement and of shortening testing time is selected at 2 MPa/s for the compression rate and also for the decompression rate.

In choosing the compression chamber diameter, the main criterion is the friction that particulate material has internally in between the particulate and between particulate and boundaries of the compression chambers. This phenomenon is known in science on powder and other particulate materials. Losses are increasing with increasing sample height. This phenomenon negatively affects the method as the actual internal sample pressure is more difficult to determine. Studies on the herein described instruments have shown that this negative effect is decreasing with increasing diameter. For carbon black particulate material, such pressure losses could be reduced to approximately 4% when using a compression chamber of about 25.4 mm (about 1 inch) diameter and a sample size of 2 grams. Further increasing the diameter does not lead to significantly improve the method, and with an even much larger diameter of about 50 mm (about 2 inches) the quality of the method decreases again when using manual techniques to fill the sample material, because material can be distributed unequally during filling.

The process can be applied for different maximum pressure values from as low as 5 MPa up to 221 MPa, when the apparatus has the dimensions as described herein. Best results, in terms of correlating void volume data to material properties of carbon black as measured by other established and industry proven means, have been achieved when using a cycle to compress up to 125 MPa.

The apparatus of the present invention is working with a compression chamber of 25.4 mm diameter, of 150 mm useable length, running material sample size of 2 grams in a test cycle at 2 MPa/s compression rate up to 125 MPa maximum pressure, holding the position for 5 seconds, and then decompressing at a rate 2 MPa/s until the initial position of the piston is reached again. The method is however not limited to these parameters.

The 1 inch diameter is not critical, because samples tested using a larger compression cylinder having a diameter of about 1 inch (about 25 mm), compared to prior art systems that use 0.5 inch (12.7 mm) cylinders. With the present invention, the size is preferred, and some variance can be done without departing from the spirit of the present invention. The choice of the 1" cylinder will significantly reduce the effect of friction material-to-cylinder compared to the 0.5 inch of other systems, which is critical as the friction creates pressure loss between the moving piston and the stationary cover. Thus, the diameter need not be exactly 1". For example, a diameter of 2" would work, but as the size is increased, there are disadvantages such as the need for an oversized machine, additional material costs, and the like.

The sample size has been chosen so to keep the above mentioned material friction low. For example, typically a 2 g sample is used for the 1" diameter cylinder. It was noted that the larger the sample, the higher is the pressure loss between piston and cover of the apparatus.

The software used to control our apparatus and make the calculations is based in part upon the algorithms that determine the void volume based upon the volume and force of the sample. The apparatus of the present invention measures the volume and the force of the sample during compression and decompression. The software accurately controls the movement of the piston and acquires force and sample thickness values from the sensors. Thickness is converted to volume and the total actual volume is converted to void volume by deducting the theoretical volume of the pure carbon (chemically=C). The remaining volume of the void (=air between solid particles) is divided by the mass in 100 g giving the void volume expressed in $cm^3$ of void per 100 g of carbon black. The force in Newton is divided by the piston surface in $mm^2$ to give the pressure in MPa. With the help of the algorithm that is applied to the decompression curve, a determination is made of the residual void volume VV_res, which is the void volume when the sample is again totally expanded, i.e., when the piston is losing contact with the sample in its down movement. So the residual void volume is the remaining volume of the sample after compressing and decompressing (again, expressed in void volume and not in absolute volume), as illustrated in FIG. 6.

The COAN value is determined by using another apparatus and the method as described in ASTM standards D2414 and D3493. It is expresses as the absorbed volume of oil in $cm^3$ of oil per 100 g of carbon black. It is commonly assumed that the void (air) in the material is in this test completely filled with oil. By comparing the VV_res values determined by the present method with the COAN values, it was determined that there was a linear correlation.

Considering the above assumption that the COAN test completely fills the void air with oil, and considering that HITEC (is the only one to) determine the void volume in its residual state (i.e. after decompression), there is a causal physical relationship between these two values.

When fillers are mixed into rubber compounds, the filler structure and the structure stability play an important role in the elastic behavior of the compounds. When subject to mechanical loads, part of the filler structure or filler network is altered, which in turn influences the properties of the compound. These softening phenomena are known in the rubber industry in the static case as Mullins effect and in the dynamic case as Payne effect.

Figure 9:
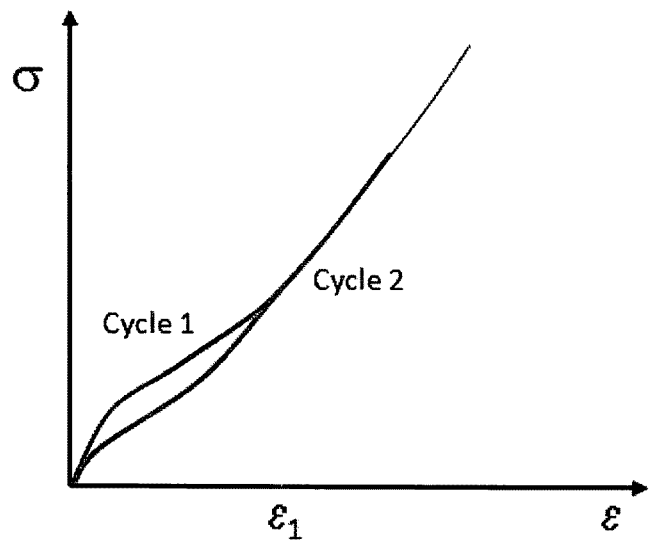
FIG. 9 is a representation of the Mullins effect, i.e. static softening of rubber compounds.

As shown in FIG. 9 (the Mullins effect), when a filled elastomer is extended to a strain 81, returned to zero strain, and stretched again, the next stress-strain curve lies below the first one, but rejoins it at 81. A possible reason for the stress softening is related to the breaking of the filler network. Another mechanism is the progressive detachment or breaking of network chains attached to filler particles.

Figure 10:
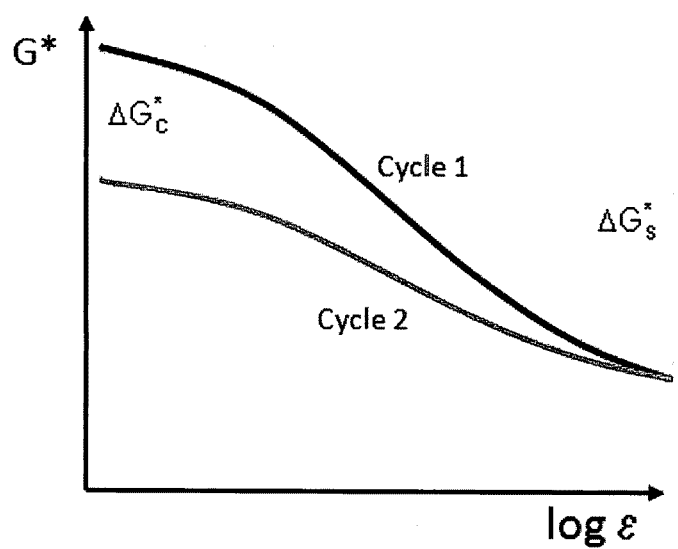
FIG. 10 is a representation of the Payne effect, i.e. dynamic softening of rubber compounds.

As shown in FIG. 10 (the Payne effect), the dynamical stiffness of filled elastomers at low amplitude deformations consists of cumulative contributions of the polymer-polymer interaction, the hydrodynamic effect, the polymer-filler interaction, and the filler-filler interaction. As the amplitude of deformation is increased, disruption of the filler-filler network causes the dynamic modulus G* to decrease.

Figure 7:
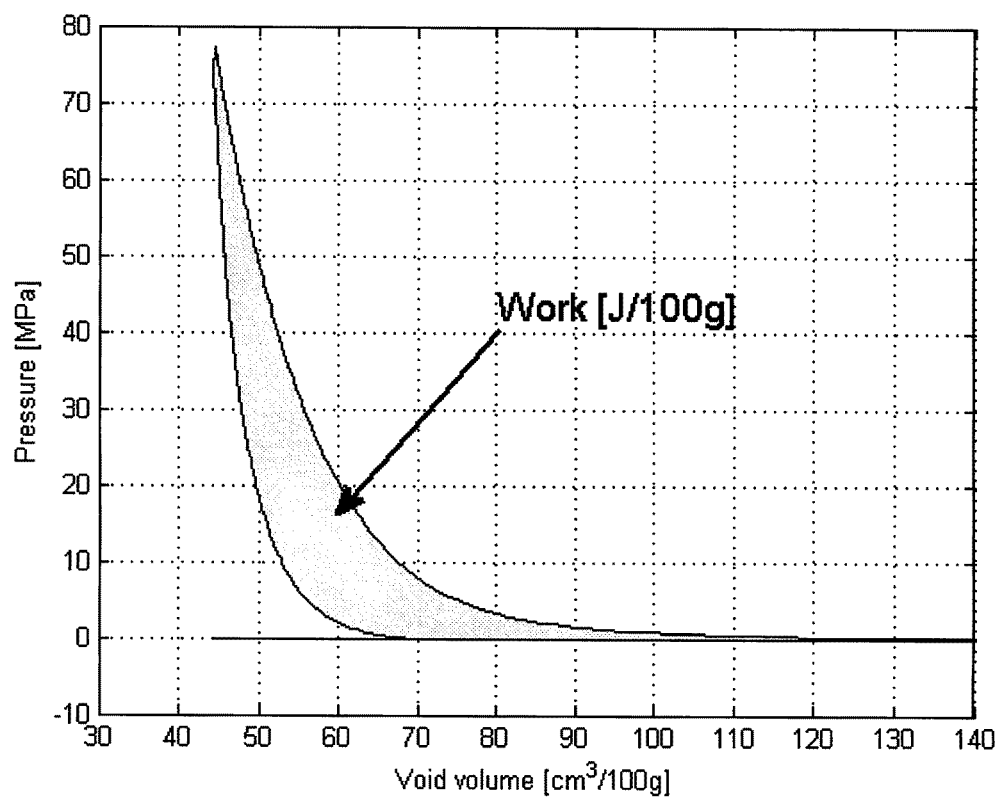
FIG. 7 is a graphical representation of the work put into a sample during a measurement cycle.

The more pronounced these effects, the more energy is required to break up the structure. As already mentioned before, the unique instrument and measurement approach of compressing and decompressing the filler samples, allows determining the stable part of the filler structure. However, the same measurement can also be used to quantify the energy required to break down the filler structure to the stable part. During a compression-decompression cycle, the moving piston puts the energy that is required to break up the structure into the sample. Graphically, this energy corresponds to the surface enclosed between the compression and the decompression curve, as illustrated in FIG. 7. From the measurement data, the energy (or work) that the piston puts into the sample can be calculated as follows:

$$W = \int p \, \partial VV = \Sigma p \Delta VV$$

i.e. the integral of the pressure over void volume, which is calculated in a numerical approach by the sum of the products of pressures and void volume increments.

Given the relationship between the Payne/Mullins effects and the energy required to reduce the filler structure to a stable part, the work determined from the void volume-pressure curves should correlate with the softening of the compounds. It has been experimentally confirmed that the work and the softening effects, i.e. the change in elastic modulus, are linearly correlated.

Thus, the unique instrument and measurement approach provide a novel and physically meaningful way of predicting compound softening with simple void volume-pressure measurements on the filler material.

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated.

What we claim is:

1. An apparatus for measuring the compressed volume of a particulate material comprising
    a chamber for containing a particulate material which will be evaluated;
    removable, fixed means at one end of said chamber to enclose said chamber and for containing said particulate material within said chamber;
    compression means at the other end of said chamber which further encloses and contains said particulate material within said chamber and which provides a linear force on said particulate material so that one end of said particulate material is linearly movable and said compression means will compress the particulate material in said chamber; said compression means comprising a movable piston;
    means for measuring the distance between said movable piston and said fixed means so to measure the thickness of said compressed particulate material; and
    measuring means on the moveable piston of said chamber for measuring the applied force of said piston to said particulate material when said piston is compressing said particulate material;
    further characterized in that
    the apparatus includes decompression means to move said moveable piston away from a particulate material placed inside said chamber to decompress the particulate material in said chamber; and
    the apparatus includes a means to control the movement of the moveable piston so that the velocity and force can be varied and controlled to be stable during compression up to a pre-set maximum force and during decompression down to full expansion and its movement during compression or decompression is smooth and continuous.

2. The apparatus of claim 1 wherein said piston has a surface which when in contact with a particulate material placed inside said chamber is linear movable and will compress the particulate material.

3. The apparatus of claim 1 wherein the compressed volume of said compressed particulate material is determined using the equation:

$$V(p) = \pi/4 * D^2 * h(p)$$

where D is the diameter of the cylindrical chamber, and where h(p) is the thickness of said compressed particulate material at pressure p as measured on said moveable piston, respectively on said fixed end at any stage of the compression or decompression of said particulate material;
    the theoretical volume of said particulate material is determined using the equation:

$$V_T = m/p$$

where m is the mass of said particulate material and p is its true (skeletal) density, which is a specific constant for every material; and
    the void volume of said particulate material is determined using the equation:

$$VV(p) = V(p)/m - V_T/m$$

where VV(p) is such expressed as per mass.

4. The apparatus of claim 2 further including a means located at the fixed end of said chamber for measuring the transmitted force on said particulate material when said piston is compressing a particulate material.

5. The apparatus of claim 1 wherein the chamber is a cylinder and the diameter of the cylindrical chamber is more than 12.7 mm (0.5 inches) and less than 76.2 mm (3 inches).

6. The apparatus of claim 1 wherein the chamber is a cylinder and the diameter of said cylindrical chamber is more than 20 mm (0.78 inches) and less then 30 mm (1.18 inches).

7. The apparatus of claim 1 wherein the chamber is a cylinder and the diameter of said cylindrical chamber is about 25 mm (about 1 inch).

8. The apparatus of claim 1 wherein the compressed volume of said compressed particulate material is determined using the equation:

$$V(p) = \pi/4 * D^2 * h(p)$$

where D is the diameter of the cylindrical chamber, and where h(p) is the thickness of said compressed particulate material at pressure p as measured on said moveable piston, respectively on said fixed end at any stage of the compression or decompression of said particulate material.

9. A method of measuring the void volume of a particulate additive material comprising
    A. providing a cylindrical chamber for containing a particulate material which will be evaluated;
    B. providing a fixed means at one end of said chamber for containing said particulate material;

C. providing a movable piston at the other end of said chamber which piston is linearly movable to compress the particulate material in said chamber;
D. providing a measuring means for measuring the force of compression of said particulate material when said piston is compressing said particulate material;
E. providing a measuring means for measuring the thickness of the compressed particulate material;
F. providing a measuring means for measuring the force of decompression of said particulate material after the release of said piston from the compressed state;
G. providing a particulate material for measurement;
H. compressing the particulate material to measure the force of compression of the particulate mass;
I. allowing the particulate material to decompress and measuring the decompression value;
J. measuring the thickness of the compressed and the decompressed material; and
K. determining the void volume of said particulate material;

wherein said particulate material is characterized as a continuous set of data points for the void volume as a function of the pressure during compression and a second set of data points for the void volume as a function of the pressure during decompression;

wherein the decompression curve is plotted using the following exponential equation:

$$p = a * \exp(b * VV) + c$$

wherein p is the pressure, VV is the void volume and a, b and c are the fit parameters, which are determined by using least squares nonlinear regression analysis on the data points for the void volume as a function of the pressure during decompression, with void volume as the independent variable.

10. The method of claim 9 wherein the data points of void volume and pressure, from pressure 10 MPa down to the end of the measurement are used for the nonlinear regression, on a system that is set to calculate pressure in MPa and void volume in cm³/100 g.

11. The method of claim 9 wherein the goodness of the fit is quantified by the coefficient of determination (the R-squared value $R^2$) as returned by the least squares nonlinear regression analysis.

12. The method of claim 11 wherein a fit is accepted as sufficiently good if its coefficient of determination (R-squared value $R^2$) is at least 0.98.

13. The method of claim 9 wherein the residual void volume is calculated using the following equation:

$$VV_{res} = 1/b * \log(q/a)$$

where q is a selected threshold from c, q must be kept constant when comparing different materials.

14. The method of claim 13 wherein the threshold q is set to 0.1 MPa on a system that is set to calculate pressure in MPa and void volume in cm³/100 g.

15. The method of claim 9 wherein the energy (or work) that the moving piston puts into the sample during a full compression and decompression cycle can be calculated using the following equation:

$$w = \int p \, \partial VV$$

and is the integral of the product of pressure p and void volume VV over the full cycle.

16. The method of claim 15 wherein said integral can be numerically solved by using the following calculation:

$$W = \Sigma p \Delta VV$$

And the sum of the products of pressure p and void volume increment $\Delta VV$, wherein the void volume increment is positive during compression and negative during decompression.

* * * * *